United States Patent [19]

Baran et al.

[11] Patent Number: 4,622,338
[45] Date of Patent: Nov. 11, 1986

[54] SUBSTITUTED GLUTARIC ACID LACTONES IN THE TREATMENT OF HYPERLIPIDEMIA

[75] Inventors: John S. Baran, Winnetka; Thomas J. Lindberg, Wheaton; Harman S. Lowrie, Northbrook, all of Ill.

[73] Assignee: G. D. Searle & Co., Skokie, Ill.

[21] Appl. No.: 710,375

[22] Filed: Mar. 11, 1985

[51] Int. Cl.⁴ .................. A61K 31/365; C07D 309/30
[52] U.S. Cl. ..................................... 514/460; 549/292
[58] Field of Search ........................ 549/292; 514/460

[56] References Cited

PUBLICATIONS

Houben–Weyl, Methoden der Organischen Chemie, vol. VI/2 (1963), pp. 778–780, 784–785.

Primary Examiner—Norma S. Milestone
Attorney, Agent, or Firm—Stuart L. Melton

[57] ABSTRACT

Compounds of formula I

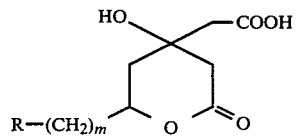

are described which are useful to inhibit the formation of serum cholesterol by virtue of their ability to inhibit β-hydroxy-β-methylglutaryl-CoA(HMG CoA), the rate-controlling substance in the synthesis of serum cholesterol.

14 Claims, No Drawings

SUBSTITUTED GLUTARIC ACID LACTONES IN THE TREATMENT OF HYPERLIPIDEMIA

BACKGROUND OF THE INVENTION

The invention relates to novel substituted glutaric acid lactone derivatives of formula I which are useful to inhibit the formation of serum lipids, and especially cholesterol. The novel compounds exhibit this utility by virtue of their ability to inhibit the activity of β-hydroxy-β-methyl-glutaryl coenzyme A (HMG CoA reductase) and thus inhibit the formation of serum cholesterol. HMG CoA is a substance which controls the rate at which cholesterol is synthesized in mammalian liver (one of the two principal in vivo sources of serum cholesterol). Thus the compounds of the present invention are useful to inhibit sterol biosynthesis in individuals predisposed to familial type hypercholesterolemia and hyperlipoproteinemia. The significance of such compounds is widely recognized, e.g. Breslow et al. Biochim. Biophys. Acta, 398, 10 (1975); Betheridge et al., Brit. Med. J., 4,500 (1975); Brown et al., Scientific American, 58 Nov. (1984).

PRIOR ART

The use of agents which lower serum cholesterol is widely described in the art as described above. 3-hydroxy-3-substituted glutaric acid derivatives are described in U.S. Pat. No. 3,818,080 as being useful for their antiulcerogenic activity.

Pentanedioic acid derivatives are described as antihyperlipidemic agents in commonly assigned co-pending application Ser. No. 577,411 filed Feb. 6, 1984, now abandoned. 3-Substituted pentanedioic hemiesters and anhydrides are described as elastase inhibitors in commonly assigned co-pending application Ser. No. 569,007, filed Jan. 9, 1984, now U.S. Pat. No. 4,554,359. In contrast, the compounds of the present invention are glutaric acid lactone derivatives which have not been heretofore suggested for lowering serum cholesterol and which are structurally unrelated to the aforementioned prior derivatives by reason of their cyclic (i.e., lactone) structures. The compounds of the invention are prepared from intermediates having a hydroxy group δ to the carboxylic acid moieties which intermediates have not been described previously.

SUMMARY OF THE INVENTION

The present invention particularly provides compounds of formula I

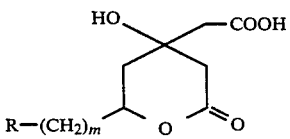

wherein
R represents lower alkyl, cycloalkyl aryl, or a group of the formula

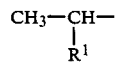

wherein $R^1$ represents cycloalkyl or phenyl;

m is an integer from 8 to 15, inclusive; and the pharmaceutically acceptable salts or esters thereof.

DETAILED DESCRIPTION OF THE INVENTION

As used herein, the expression "lower alkyl" includes straight or branched chain alkyl of 1 to 6 carbon atoms. Exemplary of suitable lower alkyl groups are methyl, ethyl, n-propyl, isopropyl, n-butyl, t-butyl, n-hexyl and the like.

Examples of suitable "cycloalkyl" groups are groups of 3 to 7 carbon atoms, including, for instance, cyclopropyl, cyclobutyl, cyclopentyl, cyclohexyl, cycloheptyl. Especially preferred in the practice of the present invention is cyclohexyl.

Suitable "aryl" groups are those of 6 to 10 carbon atoms, including phenyl and naphthyl with phenyl being especially preferred.

Appropriate pharmaceutically acceptable "salts" include $Na+$, $K+$, $Ca++$, $NH_4+$ and any other cation capable of reacting with the carboxylic acid moiety provided same does not adversely affect the pharmacological properties of the resulting compounds. Likewise, appropriate lower alkyl esters are encompassed within the scope of formula I.

Especially preferred compounds of formula I are those wherein R is a group selected from

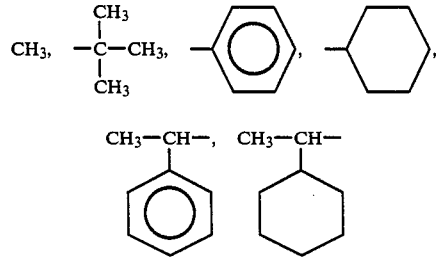

and m is an integer between 8 to 13, inclusive.

Particularly preferred compounds in accordance with the present invention are of the formulae:

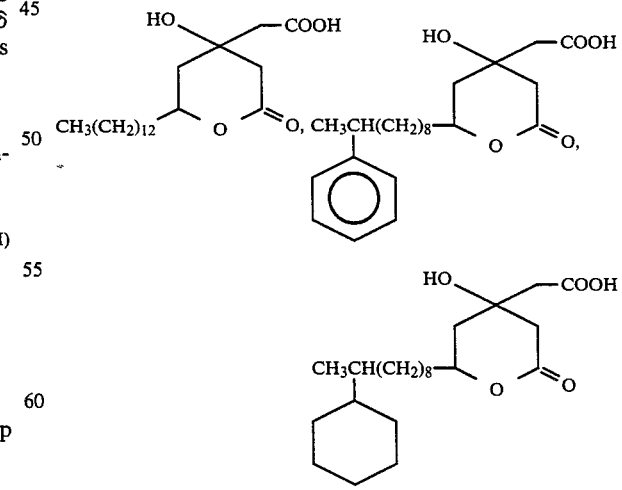

It will be appreciated by those skilled in the art that the compounds of the present invention contain asymmetric carbon atoms, (i.e., centers of chirality) and, therefore, the compounds depicted may exist as individual diastereomers or mixtures thereof and such diastereomers and mixtures are included within the scope of the defined structural formulas herein.

The utility of the instant compounds and their inhibition of the formation of serum cholesterol can be demonstrated via the following standarized test procedures:

The in vitro inhibitory activity of the present compounds is evaluated using rat liver microsomal HMGCoA reductase as described by Edwards, et al. J. Biol. Chem. 249, 2891 (1974). The $IC_{50}$ is defined as the concentration required to inhibit the enzyme by 50% of control.

HMG derivaties are added to a preincubation mixture consisting of 0.1 M K $PO_4$, PH7.2, 0.02 M glucose-6-$PO_4$, 2.5 mM NADP, 0.7 units of glucose-6-$PO_4$ dehydrogenase, 5 mM dithiothreitol, 50 mM mevalonic acid and approximately 50 μg of microsomal protein. Triplicate samples are preincubated for 15 min. at 37° C. in a volume of 1 ml. Incubation is started with 40 μM 14C-HMGCoA (0.1 ml) run for 15 min. at 37° C. and stopped with 5 N HCl (0.1 ml). Assay tubes are allowed to set for at least 30 min., then approximately 50,000 dpm of $^3$H-mevalonic acid are added to provide for extraction efficiency. Mevalonic acid is extracted with ether and the % $^{14}$C-HMGCoA incorporation determined for concurrent control and test reaction systems. Testing is done (first) with a range finding assay followed by a 4 or 5 point assay to find the $IC_{50}$ value. Coefficient of variation ranged from 5 to 20% with an average value of 14%. Compactin in this test had an $IC_{50}$ value of 1 μM under these conditions.

In vivo activity is tested as follows:

Initial serum total cholesterol, triglycerides, and lipoprotein cholesterol values are determined 3 times for each male Rhesus monkey used before treatment with a test compound begins. The test compound is administered in an initial dose of 60 mg/kg for 2 weeks and blood samples are taken to determine if rebound occurs. A dose is rated active if the 14-day mean values are significantly reduced from the pretreatment values (p 0.05). Statistical comparisons are made using the two tailed student's t test.

By virtue of their activity in the foregoing tests, the compounds of formula I are useful in treating type 2 hypercholesterolemia (TTH-2) in humans and animals. A physician or veterinarian of ordinary skill could readily determine a subject who has TTH-2 symptoms. Regardless of the route of administration selected, the compounds of the present invention are formulated into pharmaceutically acceptable dosage forms by conventional methods known to the pharmaceutical art.

The compounds can be administered in such oral unit dosage forms as tablets, capsules, pills, powders, or granules. They also may be administered rectally, intraparenterally, subcutaneously, or intramuscularly, using forms known to the pharmaceutical art. In general, the preferred form of administration is orally.

An effective but non-toxic quantity of the compound is employed in treatment. The dosage regimen for preventing or treating TTH-2 or other hyperlipidemic conditions by compounds of this invention is selected in accordance with a variety of factors including the type, age, weight, sex, and medical condition of the mammal, the severity of the condition, the route of administration and the particular compound employed. An ordinarily skilled physician or veterinarian will readily determine and prescribe the effective amount of the active agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 10 mg/kg up to 200 mg/kg orally. When other forms of administration are employed equivalent or adjusted doses are administered depending on the route of administration.

The general procedure for producing the compounds of the present invention is outlined in the following reaction scheme, which is similar to the general procedures used to produce the compounds of U.S. Pat. No. 3,818,080 which is incorporated herein by reference.

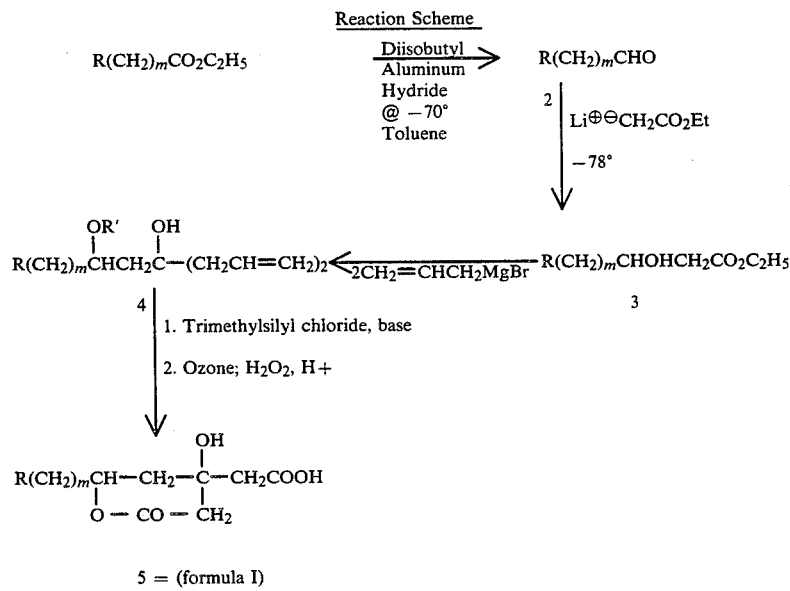

5 = (formula I)

The hydroxyacid esters 3 and the 4-allyl derivatives 4 in the above reaction scheme are novel intermediates for the synthesis of the active lactones of the present invention of formula I. In the above formulas, R' is a suitable protecting group selected in accordance with conventional practices in the art. Alkylsilyl groups, e.g. trimethylsilyl, are preferred in the present invention.

The starting esters 1 as well as the aldehydes 2 may be readily synthesized in accordance with methods known in the art or may be purchased from available sources for conversion to the novel intermediates 3.

The compounds of the present invention by reason of their serum lipid (e.g. cholesterol) lowering properties are useful alone or in the pharmaceutical compositions and methods of the invention as antihyperlipidemic agents. Ultimately the compounds of the invention find applications in the treatment, prevention or mitigation of atherosclerosis, arteriosclerosis, myocardial infarction, hypertension, and related conditions in which elevated serum lipid/cholesterol levels are a causative component.

The following non-limiting examples further illustrate details for the preparation of compounds of the present invention. The invention as a whole is not to be construed or limited either in spirit or in scope by the following examples. Those skilled in the art will readily understand that variations in the conditions and processes exemplified in the following preparative procedures can be utilized to prepare these compounds. All temperatures are degrees Celcius unless otherwise specified. Chemical shifts for NMR spectra are reported in parts per million ($\delta$). Splitting patterns are designated as s, singlet; d, doublet; t, triplet; q, quartet, and m, multiplet. Elemental analyses were performed by microanalytical procedures.

DESCRIPTION OF THE PREFERRED EMBODIMENTS

Example 1

3-Carboxymethyl-3,5-Dihydroxyoctadecanoic Acid-1,5-Lactone

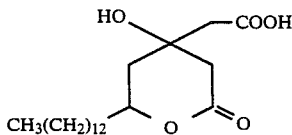

(A) 3-Hydroxyhexadecanoic acid Ethylester, (3, $R=CH_3$, $m=12$) To a freshly prepared solution of 250 ml of dry THF containing 4.41 g (0.05 mole) of lithioethyl acetate cooled to $-78°$, standing for one hour, was added, over ten minutes, a solution of 10 g (0.047 mole) of tetradecanal (2, $R=CH_3$, $m=12$) in 90 ml of THF. Then 15 ml of a 20% aqueous solution of HCl was added to the mixture, followed by water and ether. The organic layer was separated, washed with aqueous sodium bicarbonate solution, water, dried over $MgSO_4$, and distilled to dryness at reduced pressure to yield 9.4 g of product. The crude product, when purified by chromatography on silica gel utilizing ethyl acetate-hexane (15:85) as an eluant, yielded 3.7 g of pure 3-hydroxyhexadecanoic acid ethylester; $\delta$ ($CDCl_3$) 1.28(24$CH_2$), 3.98–4.33 (quartet,$OCH_2$—).

(B) 4-allyl-4,6-dihydroxynonadec-1-ene (4,$R=CH_3$, $R'=H$ $m=12$) To a small amount of freshly prepared allyl magnesium bromide and 1.7 g of Mg (0.07 mole) covered with THF was added a solution of 3.7 g of 3-hydroxyhexadecanoic acid ethyl ester (0.0123 mole) and 6.05 g (0.05 mole) of allyl bromide in 100 ml of THF. The addition proceeded so as to maintain a reflux temperature. The mixture was heated at refluxing temperature for 1 hr., cooled, and poured into saturated aq. ammonium chloride solution. The mixture was extracted with ether and the ether solution was dried over $MgSO_4$ and distilled to dryness. The crude product weighed 5.0 g and could be used without further purification. The product could be purified by column chromatography on silica gel using ethyl acetate-hexane (15:85) as the eluant; $\delta$ ($CDCl_3$), 1.28($CH_2$), 4.90–5.25(m, $=CH_2$) and 5.4–6.2(m,$=CH$).

(C) 3-Carboxymethyl-3,5-dihydroxyoctadecanoic Acid 1,5-Lactone (5, $R=CH_3$, $m=12$). To a solution of 7.7 g (0.023 mole) of 4-allyl-4,6-dihydroxynonadec-1-ene, (4, $R=CH_3$, $R'=H$, $m=12$) and 2.32 g (0.034 mole) of imidazole in 100 ml. of methylene chloride, cooled to 0°, was added, dropwise with stirring, 3.69 g (0.34 mole) of trimethylsilylchloride. A white precipitate formed. The mixture was allowed to warm to 20° and 100 ml. of water was added. The methylene chloride solution was separated, dried over $MgSO_4$, and distilled to dryness to yield 8.7 g of the crude trimethylsilyloxy derivative (4, $R=CH_3$, $R'=Si(CH_3)_3$, $m=12$) which was used without further purification.

A solution of 14.0 g of the trimethylsilyloxydiene (4, $R=CH_3$, $R'=Si(CH_3)_3$, $m=12$) in 600 ml of ethylacetate/methylene chloride (1:1) was cooled to $-25°$. Ozone was passed into the solution until it turned blue, and then the excess ozone was purged with oxygen. This cold solution was then added dropwise, with stirring, to 100 ml of glacial acetic acid. This solution was concentrated to about $\frac{1}{3}-\frac{1}{2}$ of its original volume and heated to reflux on a steam bath. A solution of 30 ml water, 80 ml glacial acetic acid, and 32 ml of 30% hydrogen peroxide, was added dropwise to the refluxing solution. The resulting reaction mixture was then refluxed for 2 hours and poured onto 400 ml of ice.

The aqueous mixture was extracted into ether, which was washed with aqueous sodium bisulfite, dried over $MgSO_4$ and distilled to dryness under reduced pressure. Trituration of the crude product with hexane yielded a crystalline material which on crystallization from methylene chloride and hexane gave 5 ($R=CH_3$, $m=12$) $R_F=0.2$ [Merck silica gel and elution with ethyl acetate-hexane (1:1), containing a trace of acetic acid]; mass spectral analysis, molecular ion=356.

Anal. Calcd. for $C_{20}H_{36}O_5$ C: 67.41; H: 10.11; Found C: 66.99; H: 10.16.

$^{13}$CMR spectrum exhibited maxima at $\delta$ 14.1 ($CH_3$); 22.7, 24.9, 29.7, 32.0, and 39.4 [($CH_2$)$_{12}$]; 39.9 and 42.2 ($CH_2$ in lactone), 45.0 ($CH_2$ attached to carboxylic acid), 68.4 (C—OH), 77.2 (C—O), 172.0 (lactone C=O), and 174.9 (COOH).

Example 2

3-Carboxymethyl-3,5-Dihydroxy-14-Phenylpentadecananoic Acid-1,5-Lactone

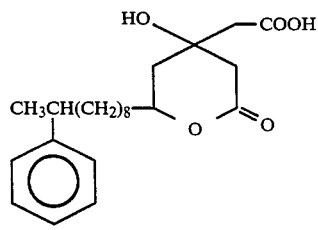

(A) 10-Phenylundecanal

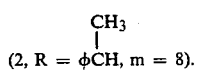

To a solution of 100 g (0.362 mole) of 11-phenylundecanoic acid methyl ester in 250 ml of toluene cooled to −78° C. was added dropwise with stirring 67 g (405 ml solution of toluene) of diisobutylaluminum hydride. The reaction mixture was stirred at −78° for 1½ hours and then quenched by adding 50 ml of water dropwise slowly and carefully, so as to prevent foaming. Then a saturated solution of 1.3 liters sodium potassium tartrate was added with stirring and the mixture was extracted with ether. The ether solution was separated, washed with water, dried over $MgSO_4$ and distilled to dryness to yield 78.5 g of the aldehyde as an oil. The compound exhibited NMR maxima at $\delta(CDCl_3)$ 1.28 (aliphatic H's), 2.,31 (−$CH_2$ adjacent to aldehyde), 7.18 (m, phenyl), and 9.73 (CHO).

(B) 3-Hydroxy-12-phenyltridecanoic acid Ethylester

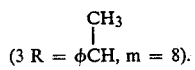

When 78 g (0.317 mole) of 10-phenylundecanal was treated with lithioethyl acetate according to the procedure for the preparation of 3(R=$CH_3$, m=12), 73.8 g (70% yield) of 3-hydroxy-12-phenyltridecanoic acid ethyl ester was obtained; $\delta$ ($CDCl_3$) 1.28 (m, $CH_2$), 2.1–2.6 (m, phenyl CH, $CH_2CO$), 3.98–4.33 (CHOH, $OCH_2$) and 7.20–7.22 (m, phenyl). This compound could be used without further purification.

(C) 4-Allyl-4,6-dihydroxy-15-phenylhexadec-1-ene

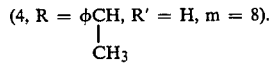

When 73 g (0.219 mole) of 3-hydroxy-13-phenyltridecanoic acid ethyl ester, 102.8 g (0.85 mole) of allyl bromide and 24.32 g (1.0 mole) of Mg was reacted as in the procedure for the preparation of 4-allyl-4,6-dihydroxyheptadec-1-ene, 74 g (90%) of product was obtained; $\delta$ ($CDCl_3$), 1.28 (m, $CH_2$), 2.15–2.60 (phenyl CH, $CH_2$, CH=), 4.90–6.2 (m, CH=$CH_2$) and 7.22 (m, phenyl).

(D) 3-Carboxymethyl-3,5-dihydroxy-14-phenylpentadecanoic acid 1,5-Lactone

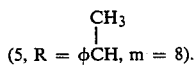

When 4.8 g (0.0129 mole) of 4-allyl-4,6-dihydroxy-15-phenylhexadec-1-ene was substituted for 4-allyl-4,6-dihydroxynonadec-1-ene in the procedure for the preparation of 5 (R=$CH_3$, m=12) 200 mg of 5

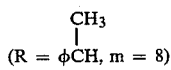

was obtained: $\delta$ ($CDCl_3$): 0.65–0.95 (m, $CH_3$), 1.28 (m, $CH_2$), 2.4–2.9 (m,$2CH_2CO$), 4.62 (m, CHOC), 7.2 (m, $C_6H_5$).

Anal. Calcd for $C_{23}H_{34}O_5 \cdot \frac{1}{3}H_2O$ C: 69.75; H: 8.73. Found C: 69.81; H, 9.03.

Example 3

3-Carboxymethyl-14-Cyclohexyl-3,5-dihydroxy pentadecanoic acid-1.5-Lactone

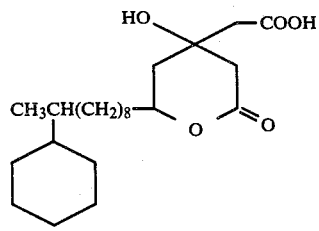

(A) 3-Hydroxy-12-cyclohexyltridecanoic acid Ethylester. 3,

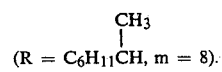

Sixty grams of 3-hydroxy-13-phenyltridecanoic acid ethyl ester in methanol solution was hydrogenated in the presence of 12 g of 5% Rhodium on carbon catalyst at 60 lbs. of hydrogen 1 $in^2$ at 60° for 25 hours. The methanol solution was distilled to dryness and the product was purified by chromatography on silica, utilizing ethylacetate-hexane (15:85) as an eluant, to yield 16.5 g of the hydroxyester; as a liquid; $\delta$ ($CDCl_3$) maxima centered at about 0.85 (m, $CH_3$), 1.28 and 1.64 (m, $CH_2$, $C_6H_{11}$) and 2.3 (m, $CH_2CO$).

(B) 4-Allyl-4,6-dihydroxy-15-cyclohexylhexadec-1-ene.

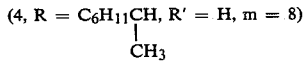

When 16.5 g (0.049 mole) of 3-hydroxy-12-cyclohexyltridecanoic acid ethylester, 20.6 g (0.17 mole) of allyl bromide and 24.3 g (0.20 mole) of magnesium was reacted as described for the preparation of 4-allyl-4,6-dihydroxyheptadec-1-ene, 14.9 g of a yellow oil was isolated in 80% yield which was used without purification; $\delta$ ($CDCl_3$) 1.28(m,$CH_2$) and 4.90–6.2(m,CH=$CH_2$).

(C) 3-Carboxymethyl-14-cyclohexyl-3,5-dihydroxypentadecanoic acid 1,5-lactone

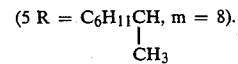

When 14.9 g (0.0394 mole) of 4-allyl-4,6-dihydroxy-15-cyclohexylhexadec-1-ene was substituted for 4-allyl-4,6-dihydroxynonadec-1-ene in the procedure for the preparation of 5 (R=$CH_3$, m=12) a yellow oil was isolated. The crude material was purified by chromatography on silica gel to yield 3-carboxymethyl-14-cyclohexyl-3, 5-dihydroxypentadecanoic acid; $\delta$ ($CDCl_3$) 0.6–1.8 (broad m, $CH_3$, $CH_2$, $C_6H_{11}$), 2.5–2.8(m,$2CH_2CO$) and 4.4–4.95(m,CH—O).

Anal. Calcd for $C_{23}H_{40}O_5 \cdot \frac{1}{3}H_2O$ C: 68.71 H: 10.11 ; Found: C: 68.82 H: 10.10.

The following data illustrate the HMG CoA reductase activity (i.e. antihypercholesterolemia or antihyperlipidemia) of the compounds of the present invention as determined in the previously identified standard laboratory test: compound of Example 1=52% inhibition at $5.0\times10^{-5}$M; compound of Example 2=57% inhibition at $5.0\times10^{-5}$M; compound of Example 3=49% inhibition at $7.5\times10^{-5}$M.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A compound of the formula

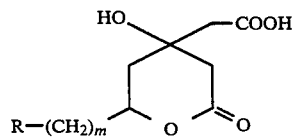

wherein
R represents lower alkyl, cycloalkyl of 3 to 7 carbon atoms, inclusive, phenyl or a group of the formula

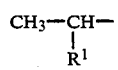

wherein $R^1$ represents cycloalkyl of 3 to 7 carbon atoms, inclusive, or phenyl; m is an integer from 8 to 15, inclusive; and the pharmaceutically acceptable carboxylic acid salts or lower alkyl esters thereof.

2. A compound according to claim 1, wherein R is methyl.

3. A compound according to claim 1 wherein R is cyclohexyl.

4. A compound according to claim 1 wherein R is the group

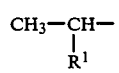

and R' is phenyl.

5. A compound according to claim 4 wherein R' is cyclohexyl.

6. A compound according to claim 1 wherein m=8.

7. A compound according to claim 1 where said compound is of the formula

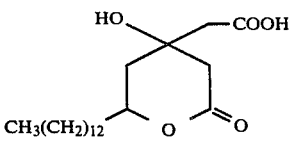

8. A compound according to claim 1 wherein said compound is of the formula

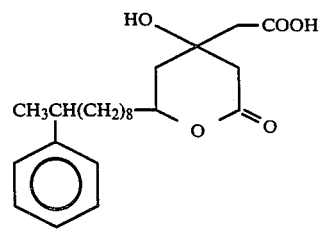

9. A compound according to claim 1 wherein said compound is of the formula

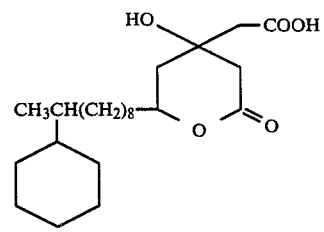

10. An antihyperlipidemic composition comprising a compound according to claim 1 in combination with a non-toxic pharmaceutical carrier.

11. A composition according to claim 10 wherein said compound is selected from a compound of the formula

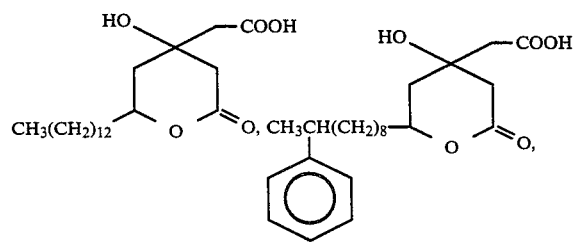

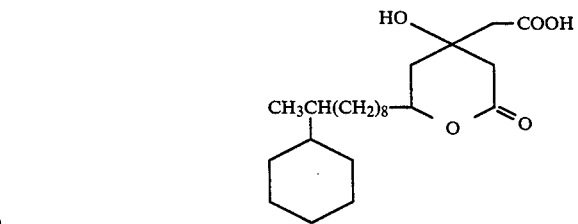

12. A method of promoting an antihyperlipidemic effect in a mammal in need thereof comprising administering thereto a non-toxic therapeutically effective amount of a compound according to claim 1.

13. A method according to claim 12 wherein said compound is selected from a compound of the formula

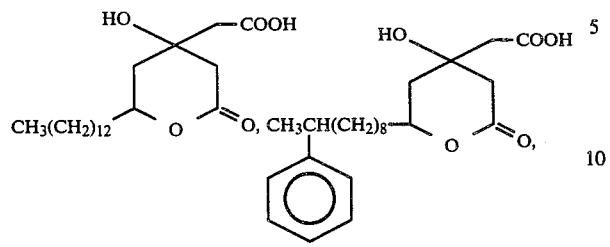
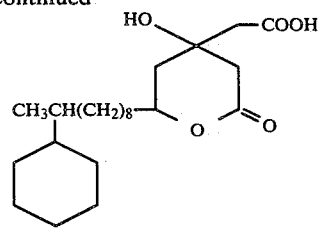
14. A method according to claim 12 wherein said compound is administered in combination with a pharmaceutical carrier in oral dosage unit form.
* * * * *